US006932768B2

(12) United States Patent
Kelly et al.

(10) Patent No.: US 6,932,768 B2
(45) Date of Patent: Aug. 23, 2005

(54) ULTRASONIC CELLULAR TISSUE SCREENING SYSTEM

(75) Inventors: Kevin M. Kelly, Venice, CA (US); Roger Royce, Venice, CA (US); Richard J. Peterson, Redondo Beach, CA (US); Luis E. Ponce, Huntington Park, CA (US); Christopher M. Underbrink, Altadena, CA (US); Matthew W. Smith, Tulsa, OK (US); Donald C. Goss, Playa del Rey, CA (US)

(73) Assignee: Sonocine, Inc., Venice, CA (US)

( * ) Notice: Subject to any disclaimer, the term of this patent is extended or adjusted under 35 U.S.C. 154(b) by 208 days.

(21) Appl. No.: 10/394,426

(22) Filed: Mar. 21, 2003

(65) Prior Publication Data

US 2004/0015080 A1 Jan. 22, 2004

Related U.S. Application Data

(63) Continuation of application No. PCT/US01/32392, filed on Oct. 15, 2001, which is a continuation of application No. 09/687,128, filed on Oct. 13, 2000, now Pat. No. 6,524,246.

(51) Int. Cl.$^7$ .............................................. A61B 8/14
(52) U.S. Cl. ...................................... 600/437; 600/459
(58) Field of Search ................................ 600/407–472; 450/36, 57; 2/237

(56) References Cited

U.S. PATENT DOCUMENTS

| 4,094,306 A | 6/1978 | Kossoff ..................... 128/2 V |
| 4,167,180 A | 9/1979 | Kossoff ...................... 128/660 |
| 4,347,850 A | 9/1982 | Kelly-Fry et al. .......... 128/660 |
| 4,489,729 A | 12/1984 | Sorenson et al. ........... 128/660 |
| 4,905,700 A | 3/1990 | Wokalek et al. ........ 128/660.01 |
| 5,152,290 A | 10/1992 | Freeland ................. 128/660.07 |
| 5,318,028 A | 6/1994 | Mitchell et al. ........ 128/660.08 |
| 5,329,929 A | 7/1994 | Sato et al. .................. 128/660 |
| 5,333,612 A | 8/1994 | Wild ....................... 128/660.9 |
| 5,433,202 A | 7/1995 | Mitchell et al. |
| 5,454,371 A | 10/1995 | Fenster et al. ......... 128/660.07 |
| 5,474,072 A | 12/1995 | Shmulewitz ............ 128/660.09 |
| 5,479,927 A | 1/1996 | Shmulewitz ............ 128/660.09 |
| 5,487,387 A | 1/1996 | Trahey et al. .......... 128/660.02 |
| 5,524,636 A | 6/1996 | Sarvazyan et al. ........... 128/774 |
| 5,562,095 A | 10/1996 | Downey et al. ........ 128/660.09 |

(Continued)

FOREIGN PATENT DOCUMENTS

| EP | 0452532 A1 | 10/1991 |
| EP | 0 882 426 A | 12/1998 |
| JP | 04 183453 A | 6/1992 |
| WO | 98 47428 A | 10/1998 |
| WO | 00/51484 | 9/2000 |

*Primary Examiner*—Ali Imam
(74) *Attorney, Agent, or Firm*—Fulbright & Jaworski L.L.P.

(57) ABSTRACT

A system for screening cellular tissue, in particular breast tissue. The system comprises an ultrasound probe that is capable of generating image data representing images of cellular tissue, one or more sensors to determine the probe's location, an image viewer, a pad, which is ultrasonically conductive and placed over the patient's nipple, and a fabric covering is placed over the breast tissue to be scanned. The pad has different ultrasonic characteristics than the cellular tissue to be scanned. The fabric covering includes an ultrasonic coupling agent and is used to hold the breast tissue in place. The fabric of the covering and the coupling agent transmit ultrasonic energy with minimal interference. The ultrasound probe is scanned over the tissue, and the one or more sensors are employed to determine the probe's location. The images representing the scanned tissue are displayed by a viewer which is capable of providing a rapid sequential display of the images.

17 Claims, 12 Drawing Sheets

U.S. PATENT DOCUMENTS

| | | | |
|---|---|---|---|
| 5,640,956 A | 6/1997 | Getzinger et al. | 128/653.1 |
| 5,664,573 A | 9/1997 | Shmulewitz | 128/660.09 |
| 5,770,801 A | 6/1998 | Wang et al. | 73/644 |
| 5,833,634 A | 11/1998 | Laird et al. | 600/587 |
| 5,842,473 A | 12/1998 | Fenster et al. | 128/660.09 |
| 5,860,934 A | 1/1999 | Sarvazyan | 600/587 |
| 5,938,613 A | 8/1999 | Shmulewitz | 600/461 |
| 5,984,870 A | 11/1999 | Giger et al. | 600/443 |
| 5,989,199 A | 11/1999 | Cundari et al. | 600/587 |
| 6,002,958 A | 12/1999 | Godik | 600/407 |
| 6,027,457 A | 2/2000 | Shmulewitz et al. | 600/562 |
| 6,117,080 A | 9/2000 | Schwartz | 600/443 |
| 6,119,033 A | 9/2000 | Spigelman et al. | 427/429 |

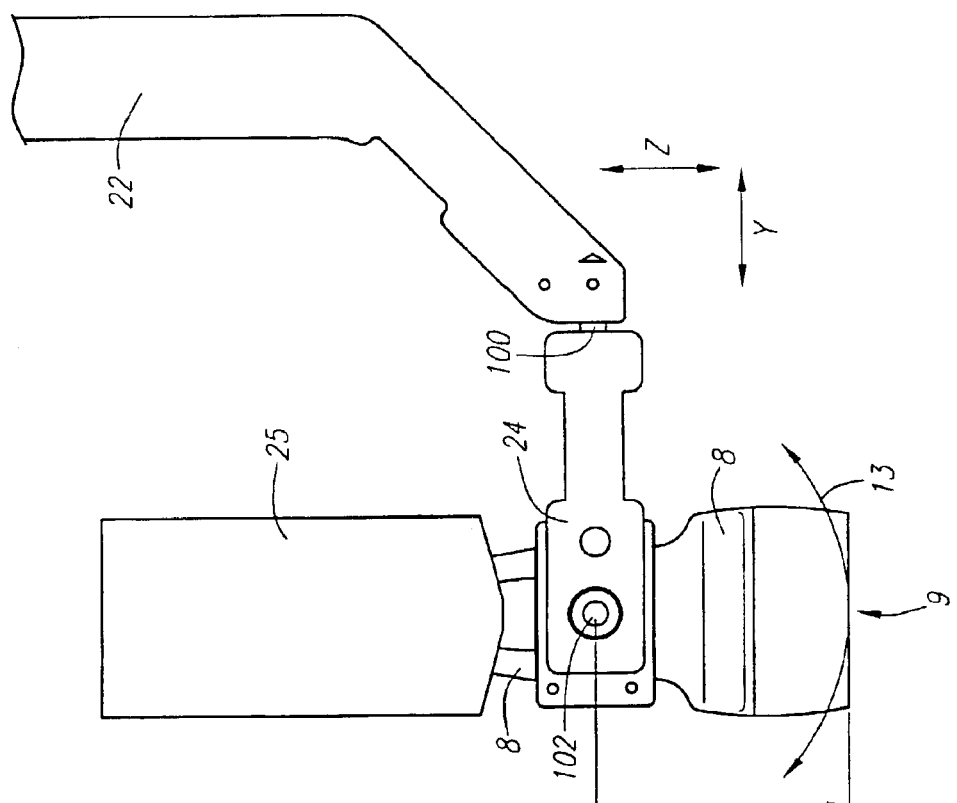
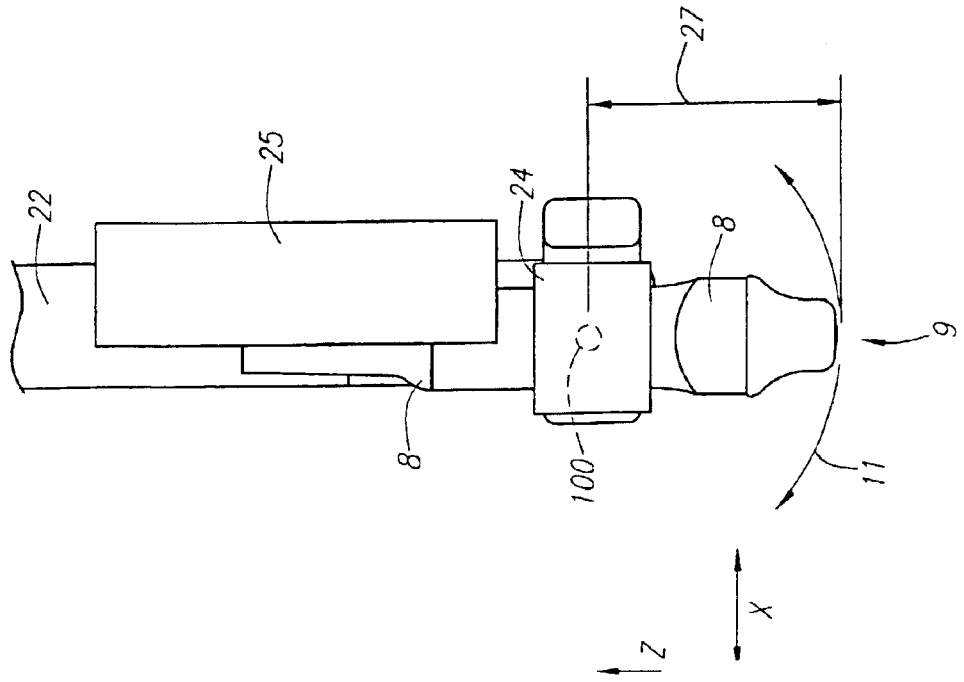

SCHEMATIC OF A PREFERRED EMBODIMENT OF A FILE THAT INCLUDES A PLURALITY OF SCAN ROW IMAGES

FILE CREATION
USER INTERFACE

PLAYBACK USER INTERFACE

POSITION CALCULATOR
IN VIEWING PROGRAM

ULTRASONIC CELLULAR TISSUE SCREENING SYSTEM

PRIORITY

This application is a continuation of International Application PCT/US01/32392, with an international filing date of Oct. 15, 2001, published in English under PCT Article 21(2), which is a continuation of U.S. Ser. No. 09/687,128, now U.S. Pat. No. 6,524,246 B1, filed Oct. 13, 2000.

BACKGROUND OF THE INVENTION

1. Field of the Invention

The field of the present invention is ultrasonic scanning and diagnostics for cellular tissue.

2. Background of the Invention

Ultrasonic probes have been used for scanning cellular tissue for many years. Presently, any medical ultrasound examination, whether of the heart, pelvis, abdomen, soft tissues or any other system, is usually displayed as a number of individual frames or pictures from a study performed in a dynamic movie-like manner. The usefulness of the scan, however, is dependent on the skill of the operator, who manipulates the probe by hand while watching the scan images on a monitor to identify areas of interest. Once these areas are identified, the operator usually records single or multiple single scan images showing those areas.

Because the operator must choose a few frames from the large number generated during the scan, the process is open to error. The operator may fail to select an image of an important finding, or may select an image that misrepresents the overall findings. In addition, since the operator is manipulating the probe by hand, and the speed of the probe over the tissue cannot be correlated with the image capture rate of the probe, the coverage of the scanned tissue is somewhat haphazard. As a result, the operator does not record a series of images that represent a contiguous and complete set of images for the entire scanned tissue. Nor does the manual operation of the probe allow for entirely uniform coverage of the tissue, even if multiple passes are used.

A second method of recording ultrasonic examinations is used for dynamic examinations such as echocardiography, where a dynamic recording is made on videotape. Unfortunately, this analog method is not matched to the digital sonographic recording of individual frames. Consequently, there is a great loss of detail that prevents the evaluation of individual frames, which limits the usefulness of the videotape for diagnosing tissue anomalies. The interpreting physician has no way to vary the speed of playback or to vary the size of the images. Nor can the physician vary the inherent contrast and brightness of the images, only the monitor settings. These difficulties lengthen the review time and prevent optimum viewing. In addition, the use of separate videotapes for individual patients is expensive, and creates a storage problem.

Specific to screening asymptomatic women for occult breast cancer, there are two methods presently in widespread use, physical examination and mammography. Both of these methods are imperfect. Physical examination usually cannot detect cancers smaller than ½ inch in diameter. Some cancers have to be many times larger to be detected. Mammography is unable to detect as many as 30 percent of cancers smaller than ½ inch. About 5 to 10 percent of larger cancers are mammographically occult. Mammograms also use radiation and necessitate painful compression of the breasts, which discourage women from having routine mammograms.

Although not well recognized by the medical community, ultrasound is very proficient at diagnosing breast cancers if the location of the abnormality is first discovered by another modality, such as mammography or physical examination. When using ultrasound as a screening method for the entire breast, however, malignancies are usually difficult to pick out of the background tissue. In the past there have been two schemes to use ultrasound for breast screening, but they failed to gain acceptance due to their unacceptably low success rate in finding cancers.

One method was a water bath system with multiple ultrasound probes and the breast in a water bath that allowed generation of images of the whole breast in consecutive slices. These slices could be viewed in sequence at a rate of one every ten seconds.

The second method was to videotape-record the scanning performed by a technician examining the entire breast. This method had the disadvantage of being somewhat haphazard in breast coverage. The variable speed of manual motion does not allow the tissue to be uniformly imaged because the speed is not synchronized to the frame capture rate of the ultrasound probe. Videotaping also results in a degradation of the images for the reasons described above.

To date, no method has been developed to uniformly and reliably use ultrasound probes to create a contiguous and complete set of scan images for an entire area of cellular tissue, such as a human breast. Ultrasound is usually used to investigate areas of interest in cellular tissue that have already been identified by other screening methods such as mammograms, x-rays, and MRI-scans. Ultrasound is not ordinarily used as a screening tool for cellular tissue anomalies.

SUMMARY OF THE INVENTION

The present invention is directed to a system for screening cellular tissue, in particular breast tissue. The system employs an ultrasound probe for generating image data representing images of cellular tissue. A pad which is ultrasonically conductive is placed over the patient's nipple. The pad has different ultrasonic characteristics than the cellular tissue to be scanned. A fabric covering is placed over the breast tissue to be scanned. The fabric covering includes an ultrasonic coupling agent and is used to hold the breast tissue in place. Further, the fabric of the covering and the coupling agent transmit ultrasonic energy with minimal interference. With the pad and fabric covering in place, the ultrasound probe is scanned over the tissue of interest, while one or more sensors are employed to determine the probe's location. The images representing the scanned tissue are displayed by a viewer which is capable of providing a rapid sequential display of the images.

The probe may be mounted on a carrier that is driven to move progressively over the cellular tissue so that the images of the cellular tissue are substantially parallel to adjacent images. Further, the carrier and probe may be motorized and a computer or microprocessor employed to control the progressive movement of the probe and carrier and/or the angular position of the probe. The microprocessor may also dynamically control the movement of the probe and carrier to maintain a uniform scan rate.

Accordingly, it is an object of the present invention to provide a system that will allow cellular tissue to be reliably screened for anomalies by ultrasonic scanning. Other objects and advantages will appear hereinafter.

BRIEF DESCRIPTION OF THE DRAWINGS

In the drawings, wherein like reference numerals refer to similar components:

FIG. 4A depicts a side view of a carrier arm and probe carrier holding an ultrasonic probe and angle sensor;

FIG. 4B depicts an end view of a carrier arm and probe carrier holding an ultrasonic probe and angle sensor;

DETAILED DESCRIPTION OF THE PREFERRED EMBODIMENT

Figure 1:
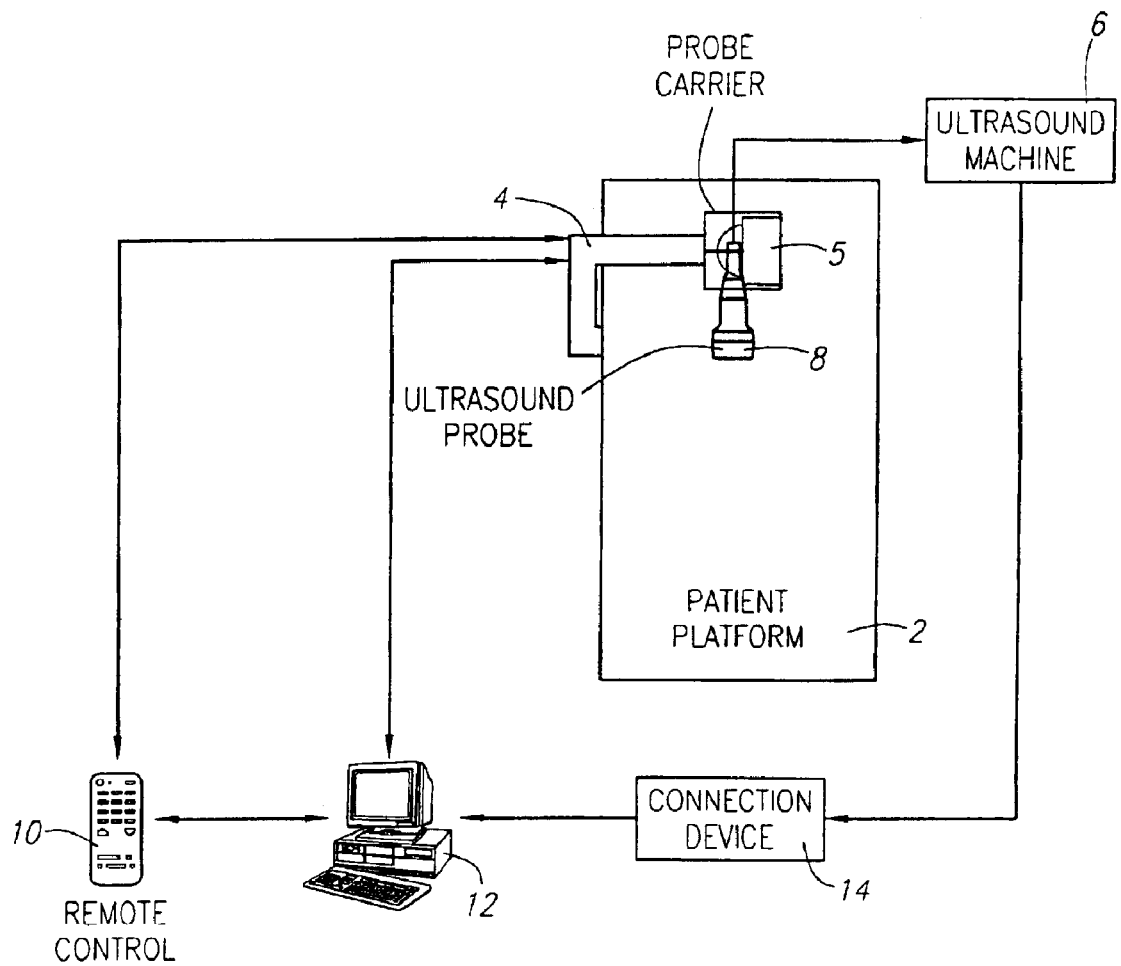
FIG. 1 is a block diagram showing the elements of a cellular tissue screening tool and its interconnections.

As shown in FIG. 1, a preferred embodiment is comprised of a patient platform 2 to steady the patient and provide a base for the support member 4, the probe carrier 5 connected with the support member 4 that is capable of translational movement to guide the probe across the tissue to be scanned, a standard medical ultrasound scanning device 6 with an associated probe 8, a remote control device 10 that operates the probe carrier 5, a standard computer 12, a connection device 14 between the ultrasound device 6 and the computer 12, and a viewing program that obtains image data from the ultrasound device and converts it into image data compatible with the viewing program and displays the images. The medical ultrasound scanning device 6 is a machine that sends and receives signals from the associated ultrasound probe 8, both of which are usually sold as a single unit. The ultrasound scanning device 6 with associated probe 8, computer 12, and connection device 14 are commercially available.

The mechanical carrier 5 holding the ultrasound probe 8 can be connected with the ultrasound scanner 6. Synchronization between the probe holder mechanical carrier 5 and the ultrasound scanner 6 can be employed while recording the scans.

1. Probe Carrier

Figure 2:
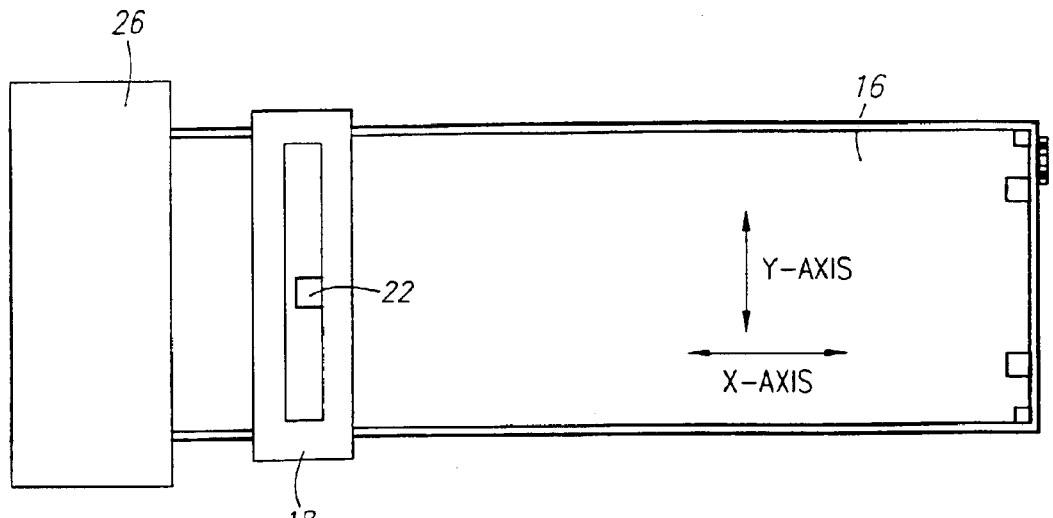
FIG. 2 depicts a plan view of a patient platform and probe carrier.
Figure 3:
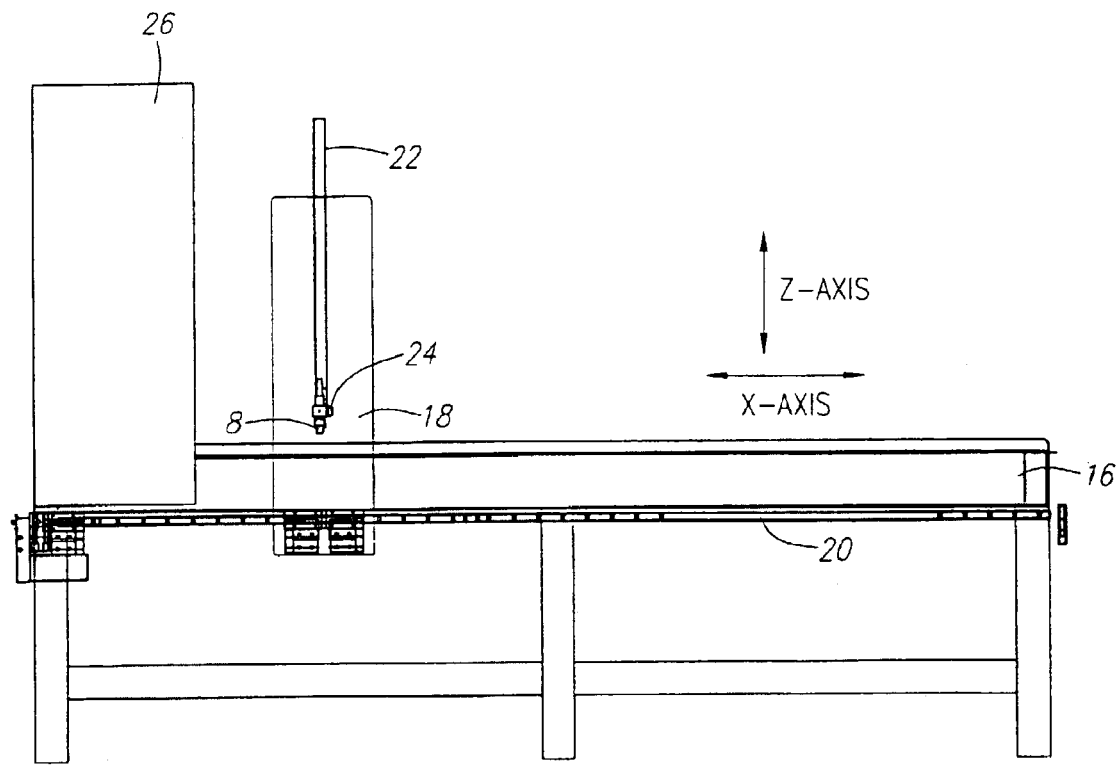
FIG. 3 depicts a side view of a patient platform and probe carrier.
Figure 4:
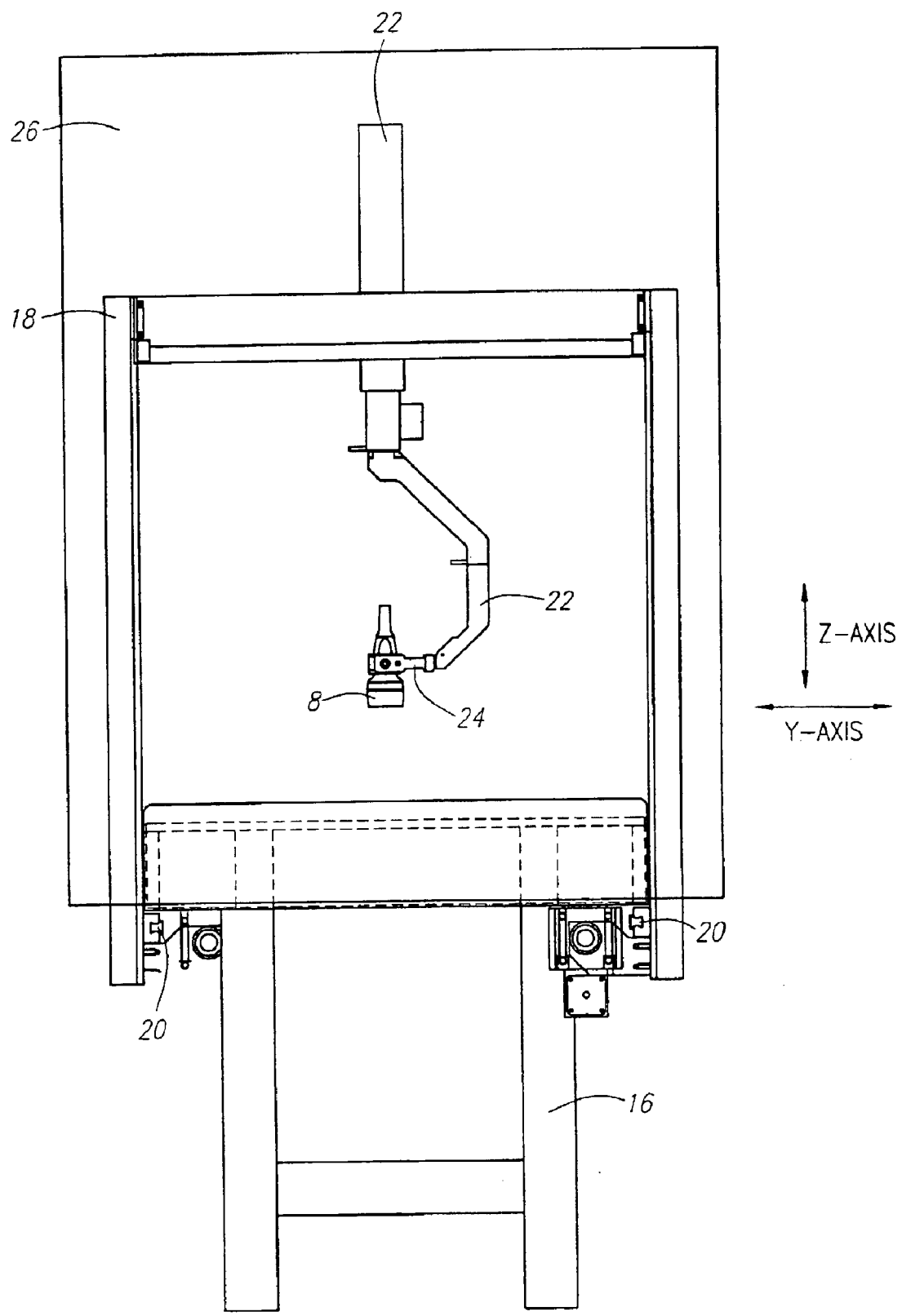
FIG. 4 depicts an end view of a patient platform, and the probe carrier holding an ultrasonic probe.

In order to obtain substantially parallel and contiguous images, a mechanical device holding the ultrasound probe 8 propels the probe across the tissue to be scanned at a uniform rate. In a preferred embodiment shown in FIG. 3, the mechanism holding the probe 8 is mounted to a patient platform 16 that steadies the patient during the exam and acts as a base for the mechanism. The carrier carriage 18 shown in FIGS. 2 and 3 is comprised of two parallel vertical members attached to rails 20 beneath the platform and a horizontal member that is attached to the top of the two vertical members, as shown in FIG. 4. The rails 20 allow the carriage 18 to move along the length of the platform, or the x-axis, as shown in FIGS. 2 and 3. Attached to the horizontal member between the two vertical members is another vertical member with an attached semi U-shaped member, called the carrier arm 22, which is attached to a carrier 24 holding an ultrasound probe 8. The carrier arm 22 is attached in such a manner that allows it to move along both the y-axis and the z-axis, so that it can move both across the patient and nearer/further from the patient on the platform, as shown in FIG. 4. The carrier 24 itself is articulated to hold the probe at any desired angle relative to the patient by rotating about the x and y axes. The carrier 24 may hold the probe 8 at a fixed angle during scanning, or can adjusted during the scanning process to keep the probe 8 perpendicular to the patient's skin (or any other preferred orientation).

To protect the carriage assembly when not in use, and to prevent the patient from becoming entangled in it when first lying on the platform, the assembly is housed in a "garage" 26 at one end of the platform 16. In a preferred embodiment, the carriage 18 is propelled along the x-axis of the platform 16 by one or more motors that are controlled by a microprocessor. The carrier arm 22 is also moved along its two axes during scanning by one or more motors controlled by one or more microprocessors. The microprocessor(s) can be separate from the computer 12 that operates the viewing program (described below), or the computer 12 can be used for this purpose. The carrier arm 22 moves along the z-axis to maintain consistent contact between the probe 8 and the patient's skin during scanning. The carrier arm 22 maintains a constant pressure of the probe 8 on the patient, with a user-selected preset value. This pressure is monitored during the scan and an override function will move the carrier arm 22 up and away from the patient in the z-axis if a maximum pressure level is detected. In another embodiment, the operator will maintain the pressure manually during the scanning process, and the pressure may be measured using pressure transducer(s) in close proximity to the probe head. The carrier arm 22 will move upward to clear the patient at the end of the scan. A manual override on the remote control 10 is also available to move the carrier arm 22 away from the patient when there is a panic or emergency situation.

In other embodiments, the carriage 18 and carrier arm 22 can be either on a parallel track arrangement (one sided or multi-sided), or be comprised of an articulating arm or some other contrivance, located over, underneath or adjacent to the patient (with or without the use of a patient platform) positioned either upright or prone. The carrier arm 22 need not be supported by a carriage assembly connected to the patient platform, but could be independently suspended from the ceiling, wall, or floor, providing translational movement in both the-x and y directions relative to the patient platform. The carrier mechanism could be similar to carriage mechanisms currently used to support x-ray machines, with means added to provide the requisite movement of the probe. The probe may be supported and propelled by a mechanical carrier by any means (manually, mechanically, electrically, hydraulically, pneumatically or by any other means, with or without control feedback), or any combination of methods. These methods, singularly or combined may be utilized to control the probe in the X, Y and Z-axes. Gravity may also be employed to provide the requisite pressure of the probe on the patient, or assist in the propulsion of the probe across the tissue.

The probe 8 may be designed as a permanent or removable component of the mechanical carrier 24. The carrier 24 may be designed with or without an onboard integrated ultrasound machine 6, ultrasound probe 8, and or ultrasound probe interface.

As shown in FIGS. 4A and 4B, the carrier 24 can be articulated to change the angular position of the probe 8 prior to or during scanning either manually, or by one or more motors controlled by one or more microprocessors. The microprocessor(s) can be separate from the computer 12 that operates the viewing program (described below), or the computer 12 can be used for this purpose. If the probe itself has an articulating head, the carrier may not need to be articulated.

In an embodiment where the probe's 8 angular position is adjusted automatically during scanning, the pitch and roll adjustments are triggered by one or more displacement transducers positioned around the ultrasound probe 8. In this embodiment, all the data related to the position and angle of the probe 8 may be provided to the viewing program to allow the images to be correlated with their corresponding location on the patient. The position data may allow the program to compensate for the overlapping of, or gaps between images. The measurement system can be by any means or convention and may consist of any or all of x, y, and z-axes and/or the probe angular position.

The speed of the carrier 24 holding the probe 8 is precisely controlled by a microprocessor. The speed may be correlated with the capture rate of the ultrasonic scanning device 6. The uniform speed of the probe face 9 over the tissue results in images that are uniformly spaced, which allows the viewing program (discussed below) to calculate the position of a selected point on any image. In an embodiment where the probe is held at a fixed angle during the scan, the uniform spacing is all that is necessary to determine the position of each frame of the scan on the patient. The ultrasound scanning device 6 may act as a controller in communication with the probe 8 to sequentially activate the probe 8 as it moves across the tissue, but any other controller could be used to activate the probe, including a computer linked to the probe or the scanning device or both.

The operator may determine the amount of area to be scanned, and input various parameters of that area into the computer's 12 positioning program. For example, when used for breast tissue scanning, the operator will measure across the skin, providing the total length to be traversed by the probe 8. In current practice, the width of the tissue scanned by the ultrasound probe 8 is generally too small to capture an image of an entire organ such as the breast. As a result, several adjacent passes are performed to provide complete coverage. Each pass (called a scan row 30) will have some overlap with the preceding pass, to achieve full coverage and eliminate the potential for missing features at the fringes of the scan. Prior to each successive pass, the carrier arm 22, lifts away from the patient, moves along the y-axis across the breast and along the x-axis to the top of the of the area to be scanned to position itself for the next scan row 30, then lowers itself along the z-axis onto the patient. Alternatively, the carrier arm 22 may be raised or lowered manually.

Figure 5:
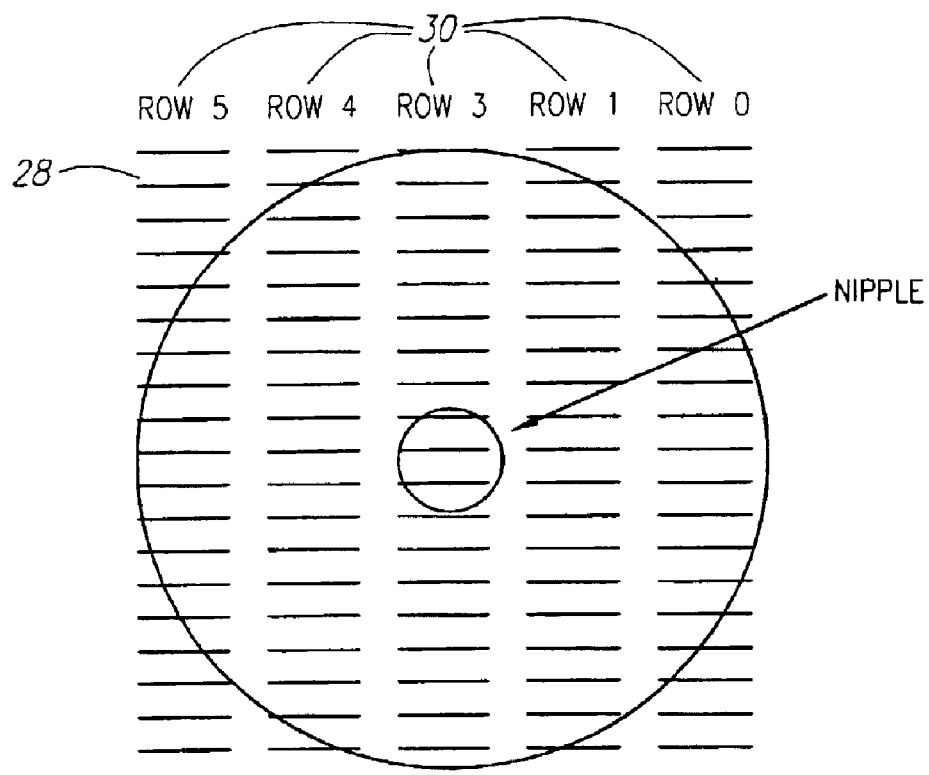
FIG. 5 is a schematic diagram showing a plurality of scan rows of scan row images of a human breast.

A scan row 30 contains a plurality of individual images or frames 28, typically about 200 to 300 for a breast. FIG. 5 depicts how the frames 28 in scan rows 30 are aligned on a typical breast scan, but for clarity, no overlap is shown. A scan row 30 can be thought of as a stack of photographic slides, each slide representing an individual frame 28. The frames 28 are evenly spaced, which may be accomplished by uniform motion of the probe 8 and uniform timing of the scans. The frames 28 are most conveniently substantially parallel to each other.

In an embodiment where the probe's angle is changed during scanning, the probe 8 is attached to a carrier 24 that allows the probe 8 to be pivoted in any direction. The roll plane 11 refers to the forward and backward pivoted movement of the probe 8 along the x-axis at the roll plane pivot 100. See FIGS. 4A and 4B. The pitch plane 13 refers to the left and right pivoted movement of the probe 8 along the y-axis at the pitch plane pivot 102. The pitch and roll pivots 100, 103 allow the probe to maintain full contact between the probe face 9 and the skin surface by allowing the probe 8 to be positioned at a perpendicular angle to the skin regardless of skin contour, to allow for optimal ultrasonic imaging. A commercially available angle sensor 25 may be attached to the carrier 24 so that it is parallel to the probe 8 at all times in both the roll plane 11 (x-axis) and the pitch plane 13 (y-axis), see FIGS. 4A and 4B. The angle sensor 25 sends the roll and the pitch angles to the positioning program in the computer 12 at short regular intervals, one tenth of a second in a preferred embodiment. FIG. 15 is a schematic diagram of the signals between the angle sensor, the computer and the motors.

Where the probe 8 is dynamically angled as the probe 8 is moved over the tissue, particularly where the tissue is not flat, several problems arise in achieving proper speed and location during the scan. For example, when trying to uniformly scan a convex object, such as a breast, the degree of convexity of the breast is unknown in both the 'x' and 'y' axes. Using a breast as an example, if the probe 8 is propelled at a constant speed along the x-axis, the speed of the probe face 9, in reference to the skin, will increase on the upslope and the downslope of the breast. In addition, since the roll plane pivot 100 in the carrier 24 is some distance above where the probe face 9 touches the skin (called the fulcrum length 27), the probe face 9 and the carrier 24 will not be in the same position along the x-axis when the probe 8 is pivoted in the roll plane. Thus the carrier 24 will be behind the probe face 9 on upslopes and in front of it on downslopes.

Location sensors could be used to track the location of the carrier 24, and the angular position of the probe 8, for accurate location and speed corrections. Sensors may determine the carrier's 24 location by counting the number of rotations of the motors controlling the movement of the carrier arm 22 in the 'x' and 'y' directions. The probe's 8 angular position may be determined by the angle sensor 25. These location sensors are "coupled" with the probe even though no direct connection to the probe may exist.

Speed correction over the skin may be implemented with an angle sensor 25 attached to the probe 8 that sends the probe's 8 angle in both the 'x' and 'y' axes to the controlling computer 12 continuously, at least ten times per second. The change of angle in the 'x' axis may be used to properly adjust the velocity for the next increment of time by applying a two-term trigonometric formula. The first term maintains a constant speed along the skin by decreasing the horizontal speed of the carrier 24 as the probe 8 gains vertical speed by climbing or descending along the slope of the breast. The second term accounts for the effect of the pivot in displacing the carrier arm 22 relative to the probe face 9. Therefore, the angle sensor 25 provides angle data to the positioning program residing on the computer 12, which controls the x-axis motor to produce uniform velocity of the pivoted probe 8 over the skin of the breast, while continuously changing only the horizontal (x-axis) velocity. To produce the desired constant velocity, the positioning program uses the cosine of current roll angle to calculate the x-axis motion vector. The positioning program also compensates for the horizontal component of the offset of the carrier 24 from the probe face 9 produced by the position of the roll plane pivot 100 in the carrier 24 being above the probe face 9. The positioning program uses the absolute change of the sines of the roll angle between the present angle and the angle in the previous time interval, using the following formula:

$$HV=(DV^*\cos(NRA)+(FL/TI^*(|\sin(ORA)-\sin(NRA)|)),$$

where:
- HV=Horizontal Velocity (of the carrier arm 22 necessary to produce DV at the present roll angle);
- DV=Default Velocity (desired velocity of the probe face 9 over the skin);
- FL=Fulcrum Length (distance between the roll plane pivot 100 and the center of the probe face 9);
- TI=Time Interval (time in seconds between angle measurements);
- ORA=Old Roll Angle (Angle of probe 8 along x-axis in last time increment); and
- NRA=New Roll Angle (Angle of probe 8 along x-axis at present).

If the computer 12 clock and the software that receives signals from the angle sensor 25 are not precisely matched, the time intervals (TI) in the above equation can be slightly different. Although in a preferred embodiment the cycles are sufficiently long to cancel out each of the small differences, to prevent errors introduced by these variable length time intervals, an additional correction factor can be used. Velocities can be requested for set intervals to achieve specific distances along the x and y-axes, but the inexactness of the time intervals may result in approximate rather than exact distances with each move. These small errors summated over an entire row could be significant and result in errors in row length and width. The solution is to interrogate the exact position of the probe 8, along the length of the x and y-axes after each time interval, and correct any small error during that time interval and convert that distance into a velocity to be added or subtracted during the next time interval. The positioning program records the number of rotations of the motors driving the horizontal (x-axis and y-axis) motion, from which the exact position of the probe 8 can be calculated.

The fact that the probe can be angled in the pitch plane 13 creates an additional lateral correction factor, using data from the location sensors. Like the roll plane pivot 100, the pitch plane pivot 102 is above the probe face 9, so any angulation in the y-axis as a result of the curvature of the tissue, such as on a breast, will cause the probe 8 to deviate from its straight-line course. If this lateral movement is not corrected, it will result in a curved row, and gaps in tissue coverage. Again, using the change in angle sent by the angle sensor 25 and a one-term trigonometric formula, the positioning program on the computer 12 can signal a y-axis motor to continuously change the lateral position of the probe 8 to maintain straight rows. To maintain straight travel over a convex surface, the positioning program calculates the correction of the y-axis position, using the change of the sines of the previous and the present pitch angles. The effect of canting the probe 8 in the pitch plane 13 adds another term to compensate for additional movement of the probe. This term is subtracted from the first term, and is the change of the cosines of the previous and the present pitch angles, using the following formula:

$$YCD=(PFW^*(\sin(OPA)-\sin(NPA)))-\tfrac{1}{2}PFW^*(\cos(OPA)-\cos(NPA)),$$

where:
- YCD=y-axis Correction Distance (of the probe 8 to correct for the offset from the change in y-axis angle from the previous time increment);
- PFW=Probe Face Width (width of the probe face 9);
- OPA=Old Pitch Angle (Angle of probe 8 along y-axis in last time increment); and
- NPA=New Pitch Angle (Angle of probe 8 along y-axis at present).

To maintain complete coverage, the carrier 24 must move the width of the probe face 9 over the skin, rather than along the 'y' axis, when beginning its next row. The sensors may be used to provide location data to the positioning program, which continuously records the maximum y-axis angle and uses the maximum angle in each row in a one-term trigonometric formula, and calculates the distance to move the probe 8 along the y-axis so that no skip area will occur. To assure that no tissue will be skipped, the rows overlap slightly, and the initial starting position of each row should be calculated to assure overlap. The positioning program uses the difference of the sines of the initial pitch angle and the maximum pitch angle in a row to calculate the distance to move the carrier 24 on the y-axis to begin the next row, using the following formula:

$$NRO=(\cos(MPA)^*PFW)-OA,$$

where:
- NRO=Next Row Offset (of the probe 8 to avoid skip areas);
- PFW=Probe Face Width (width of the probe face 9);
- MPA=Maximum Pitch Angle (in the present row); and
- OA=Overlap Amount (of the contiguous rows).

In the embodiment where the probe's 8 angular position is dynamically adjusted during scanning to follow the contours of the tissue being scanned, the tops of the frames 28 are substantially evenly spaced, and the tissue contours will be sufficiently gentle that adjacent frames 28 will remain substantially parallel to each other, although they may differ by as much as a few degrees. Although adjacent frames 28 within a single scan row 30 are substantially parallel, frames 28 may become progressively less parallel as they are separated by an increasing number of frames 28. Frames 28 in two adjacent scan rows 30 are not necessarily substantially parallel.

In a preferred embodiment, an organ such as a breast can be scanned in one segment, with the scan rows 30 progressing across the entire breast from lateral to medial, or vice-versa. FIG. 5 depicts a series of scan rows 30 comprising one segment. In other embodiments, each breast may be scanned in two segments, with the first scan row of each segment aligned at the center of the breast at the nipple and successive scan rows 30 being progressively further from the nipple.

2. Viewing Program

A preferred embodiment of the viewing program (or viewer) is a streamlined, monolithic, 32-bit Windows application designed to run on Windows 95, Windows 98, NT 4, and Windows 2000. A preferred embodiment is implemented to interface with and acquire data from the General Electric Logiq 700 medical ultrasound scanner. The viewing program could, of course, be written to run on other types of computer systems and future versions of operating systems, and to interface with other types of scanning devices. As used in the claims, "computer" generically refers to any suitable device using one or more microprocessors to process data.

The viewing program's monolithic structure and relatively small size allow it to be bundled with the image data for ease of transport and viewing flexibility. In most cases, complete scan data for a patient and the program can be placed on a single CD, allowing the user to transport a number of patient scans in a relatively small package, and view them on any computer that is compatible with the software on the CD. Although it would be even more convenient to transmit scans via e-mail, the current speed and size limitations of e-mail make sending the entire scan impractical. If desired, however, the viewing program can select small segments of the scan data and bundle it with the viewing program, for a small data package that is practical to send via current e-mail systems. Other delivery options could also be utilized, such as streaming video over the internet, or discrete file downloads using file compression to speed download time. In addition, the viewer can export or print single frames 28 in a standard image format, such as bitmap.

In other embodiments, the viewing program could be designed to operate solely on a computer on which it resides, or it could be resident on a server in a client-server environment. The program could also be non-monolithic, using Java or a similar language, in a network-centric environment.

In a preferred embodiment shown in FIG. 1, the viewer program controls the scanning operation and data offloading via a connection device 14, such as a network TCP/IP interface. Other connection devices could be used, or with certain scanners, none may be needed. The General Electric Logiq 700 ultrasonic scanning device has an internal buffer that can store a finite amount of image data before offloading is required to clear the buffer for another scan. Other scanning devices have no such buffer, but instead provide an output of streaming data as the scan is being performed, and the program is capable of acquiring image data from a variety of scanning devices.

Figure 6:
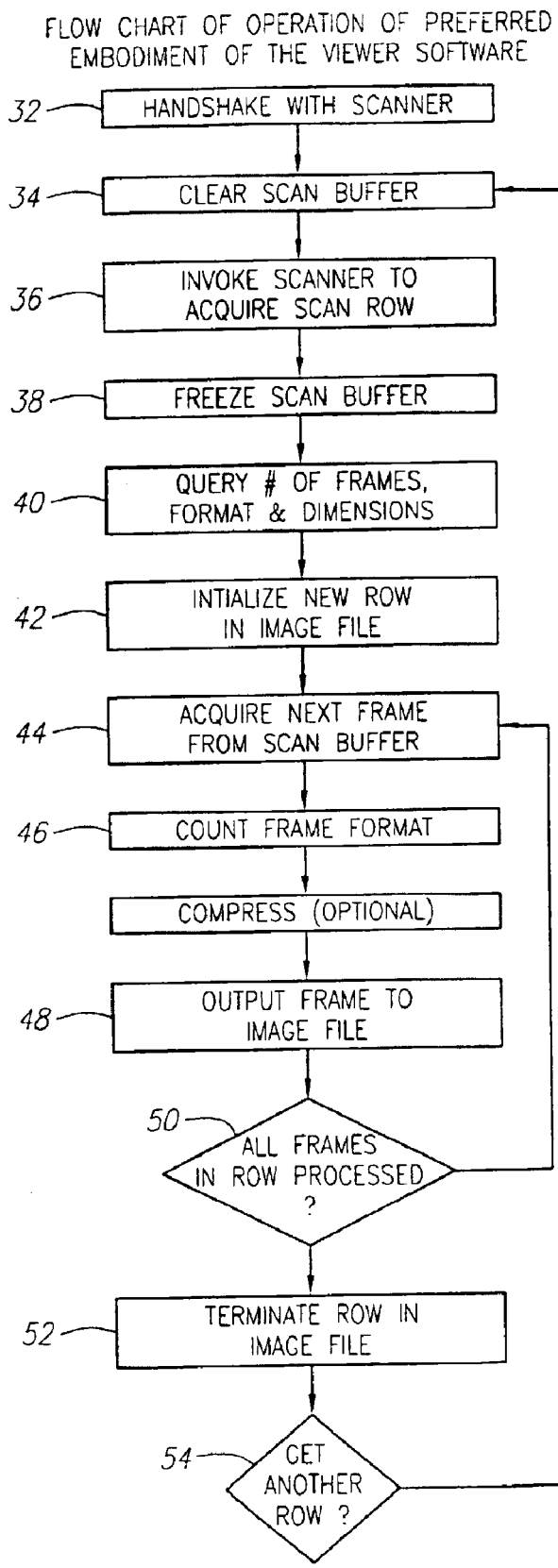
FIG. 6 is a flow chart describing how the viewing program on the computer acquires data from the ultrasonic scanner, converts it into digital image data that can be used by the viewing program, and creates an image file.

In a preferred embodiment, the computer acts as a receiver and recorder for the ultrasonic images obtained from the ultrasonic scanning device. As shown in FIG. 6, a preferred embodiment uses a handshake sequence between the viewer and scanner to begin the scan acquisition process 32. The viewer then invokes the scanner to clear its internal frame buffer 34 and then to acquire a scan row to its internal buffer 36. The viewer freezes the scanner buffer 38, determines the number of frames 28 in the buffer, their dimensions and pixel format 40, initializes a new scan row in the image file 42, reads individual frames 28 from the buffer 44, counts the frame format 46 and writes them into the image file 48 on a data storage device. It then repeats the acquisition process until all the frames 28 in the scan row are processed 50, and terminates the scan row in the file 52. It then starts all over with additional scan rows 30 until the entire scan is acquired in the image file 54. A preferred embodiment of the viewer uses a proprietary image file format, which contains a header for patient information and scan information ("image file"), but images could also be converted into standardized formats such as DICOM.

Figure 7:
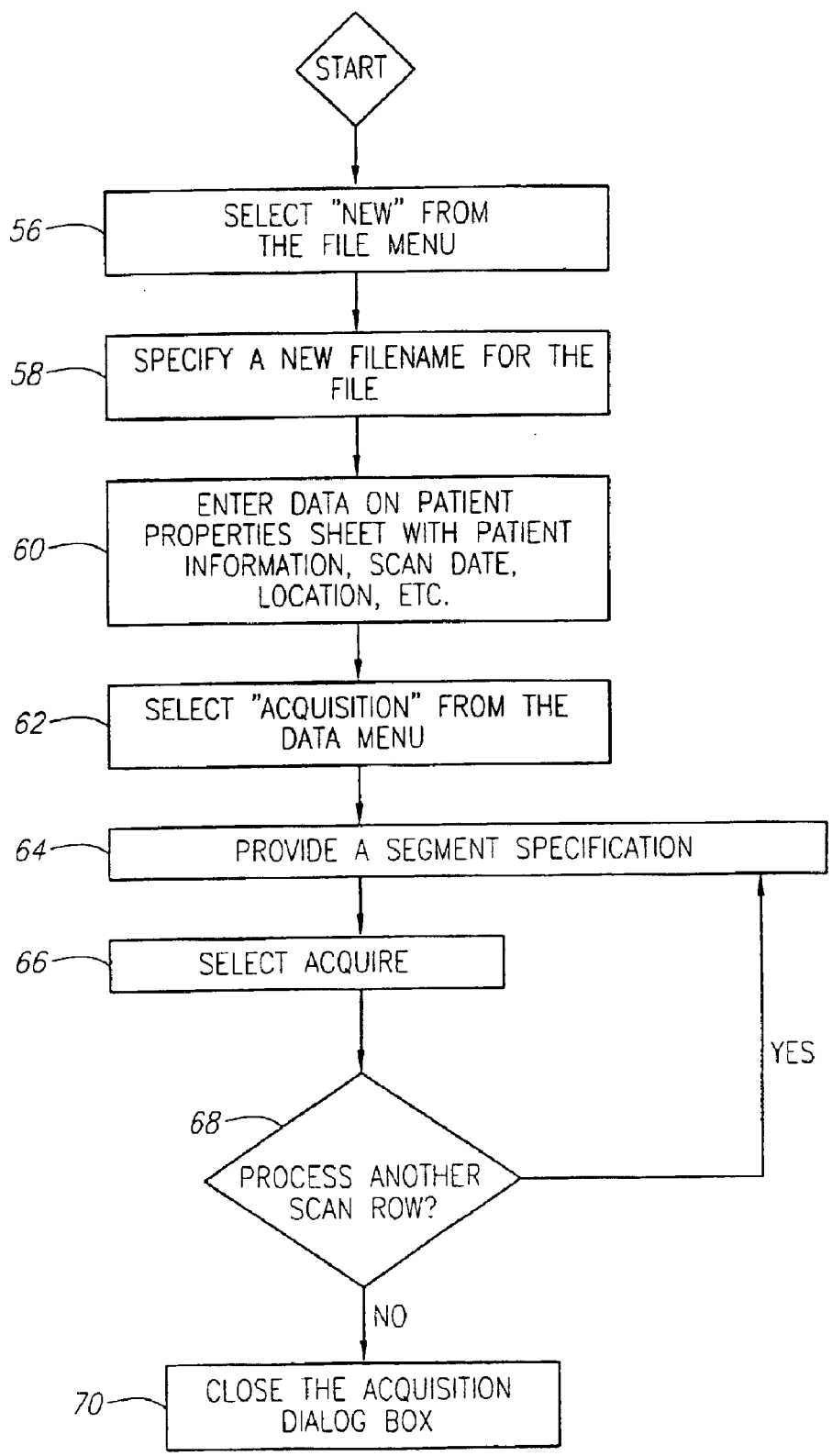
FIG. 7 is a flow chart describing how a user interface of the viewing program operates to acquire data from the ultrasonic scanner and create an image file on the computer.

FIG. 7 is a flow chart showing the user interface for the data transfer process from the scanner to the computer. The user creates a new file by choosing from the file menu 56, specifies a name for the new file 58, enters the patient data and relevant information 60, makes a selection from the data menu 62, and specifies what segment of the breast is about to be acquired 64. The user then begins the acquisition process 66, and frames 28 are then offloaded sequentially from the scanner's frame buffer via a connection device 14, such as a network interface, then normalized, compressed losslessly (if desired) and written sequentially to the image file, said file recorded on a data storage device. When all buffered frames are processed, the viewer terminates the constructed row in the image file 68. Another scan row can then be acquired and so on, or the interface to the scanner may be terminated 70. For offloading streaming data, the program performs a real-time write-through.

3. Acquiring the Data

Figure 8:
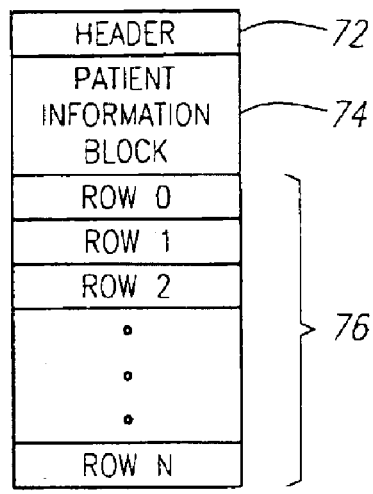
FIG. 8 is a schematic of a preferred embodiment of an image file containing a plurality of scan row images.

In a preferred embodiment, the viewer creates (and subsequently displays) proprietary image files, the format of which consists of a file header 72, a patient information block 74, and zero or more blocks of scan row frames 76, as shown in FIG. 8. The patient information block 74 contains not only information about the patient, but also information about the scan itself, such as the depth and width of the scan, length of the scan row, speed of the carrier 24 during the scan, the number of frames per second captured by the scanner, the spacing between each frame, etc.

In another embodiment where the probe's angular position is dynamically adjusted during the scan, the viewer program may record on a data storage device the angular position of each frame and other information for each frame. The angular position data can be provided to the viewer program though the scanner 6, from angle sensor 25 attached to the probe 8 or the carrier 24, or from an intermediary computer program that gathers this data.

The viewer is implemented to be largely independent of the particular scanner hardware with which it is paired. A specific module written for each scanner is responsible for "normalizing" data from the internal format used by that particular scanner to the format used within an image file. The computer acts as a conversion device to convert this scanner data into the viewer's image file format. Scan row frame elements stored in an image file are written in a format optimized for rapid rendering during display. In a preferred embodiment, the viewer is run on computers using a WIN 32 operating system, and scan frames 28 are written to image files in an 8-bit format that closely mirrors 8-bit grayscale Windows DIB (device-independent bitmap) format. This allows the images to be efficiently displayed on a Windows computer with practically no routine translation.

4. Displaying the Images

After acquiring, converting, and storing the scan data, the second major task of the viewer is to display the scan images. The viewer opens a previously created image file and renders sequential scan row frames within its interface in a "movie-like" manner. The images can be played at variable speed, backward or forward, and can pause on a single frame.

Figure 9:
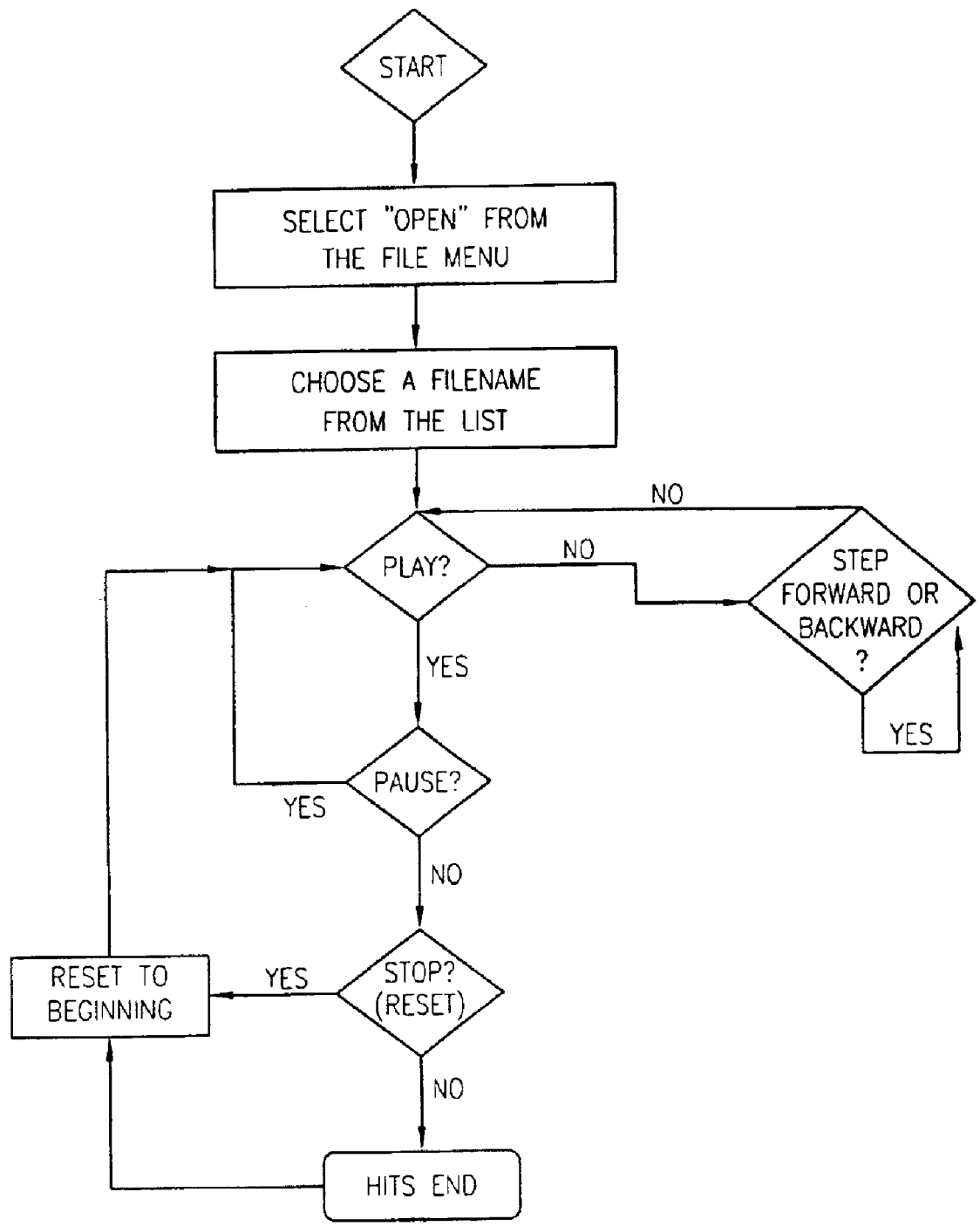
FIG. 9 is a flow chart describing how the user interface of the viewing program operates during playback of images on the computer.

The user interface for the viewing program may look and operate in largely the same manner as commercially available digital video players, such as Microsoft Windows Media Player, with buttons for Play, Pause, Stop, a slider bar to move back and forth within segments, etc. The playback features may utilize standard Windows input/output operations commonly used in digital video applications. A generalized flow diagram showing the user interface steps for playback operation is shown in FIG. 9.

One of the viewer features is a location function, which determines the physical location (on the patient) of any point on any frame 28 given any selected reference point on the same frame, or on a different frame. For example, if a physician finds an abnormality on one frame, he needs to then be able to locate some prominent feature elsewhere in the frame data, i.e., the nipple or a temporary mark placed by the operator, and then find the position of the abnormality relative to that reference point.

Figure 10:
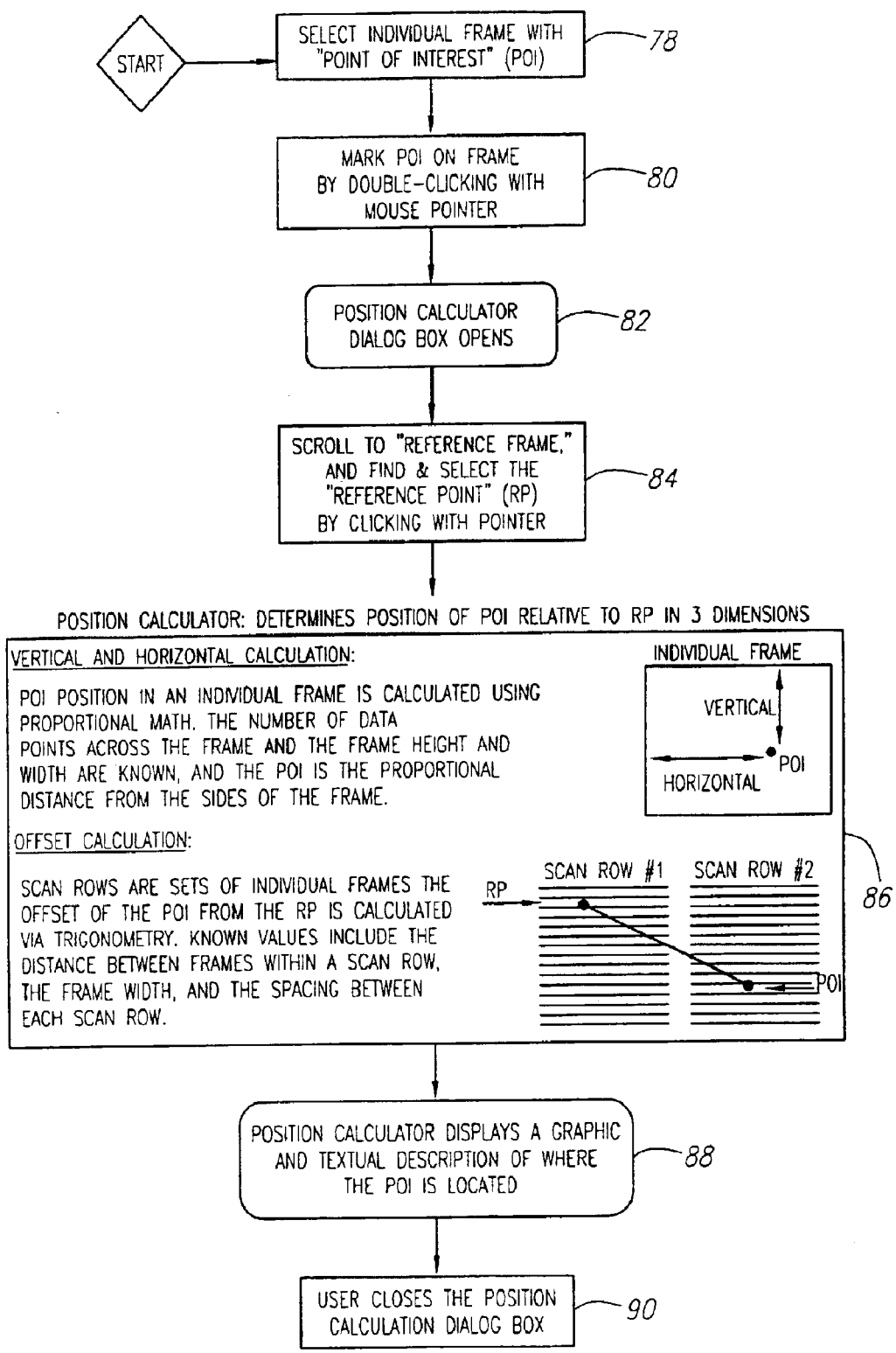
FIG. 10 is a flow chart describing the operation of the viewing program's location function.

The user interface for the location feature operates as shown in the flowchart in FIG. 10. The user marks the point-of-interest ("POI") on a particular frame 28 being viewed 78 by double-clicking it with the computer mouse 80. An overlapped window then appears, and within that window a small display pane shows "thumbnail"-sized sonograph frames taken from the scan rows (actually, the same row "segment") in which the abnormality lies 82. The user can then traverse through the thumbnailed frames until he locates a reference frame containing a reference point ("RP") he wishes to use 84. In the case of a breast scan, the RP will often be the nipple, which can be positively identified by placing a special pad 120 over the nipple during the scan, readily identifiable on the viewer image. The user can then mark a point on that reference frame using the mouse 84. The viewer program immediately calculates the first position relative to the reference point 86 and displays the results (in both textual and graphical format) to the user 88. The user then closes the dialog box to end the function 90.

To implement the location function, the viewer takes advantage of the data known about the scan, which is written in the image file's header as part of the data acquisition process. Such information includes the width of the frame, and the distance between subsequent frames in a particular scan row, and the offset between scan rows. Within an individual frame, the location function calculates the position of a user-selected point by proportional math, using the number of image data points (pixels) in the height and width, and the size of the frame, to calculate the distance of the point from the sides of the frame. The program counts the number of pixels across the width of the frame, then the user-selected pixel position number is multiplied by the frame width and divided by the total number of pixels. For example, assuming the frame width is 4 centimeters, the program counts 400 pixels across that width, and the user selected a point at pixel position 100: 100 * 4 cm/400=1 cm. So the selected point is 1 centimeter from the side of the frame. The program then performs a similar calculation to determine the selected point's distance from the top of the frame. FIG. 10 depicts this process and also shows how the location function determines the distances and angles from a user-selected point of interest (POI) to a user-selected reference point (RP), using the known values and simple trigonometry 86. In breast cancer screening, the POI is usually a suspected cancer, and the RP is the nipple.

The substantially uniform motion of the probe 8 results in evenly spaced frames 28, and thus the distance from a reference frame to a particular frame is calculated by counting the number of frames between them and multiplying by the spacing 86. In addition, the overlap of each scan row is known, and thus if the RP is in a different scan row than the POI, determining the location is a simple matter of determining the overlap and measuring the distance, and using trigonometry to make any angular and remaining distance calculations 86. Therefore, counting the frames from the RP and taking into account their overlap provides the location of each individual image.

In a preferred embodiment where the angular position of the probe is dynamically adjusted during the scanning process, the viewing program may obtain each frame's angular position during the scan from the angle sensor 25, along with the other information described above. Using that information, the location function may again use simple trigonometry to calculate the distances between the RP and the POI.

Another feature of the viewer is its ability to accurately measure the distance between two user-selected points on a single frame. This allows the user to measure anomalies or features found in the images. The process for measuring is very similar to the location function process. Using the known values for frame depth and width, the measuring function uses proportional math to determine the distance between the two points. To measure diagonally across a frame, proportional math is used to determine the lengths of the triangle legs, and simple trigonometry is used to calculate the length of the hypotenuse, which is the distance between the points.

5. Carrier-less Embodiment

It is possible to obtain the sequential scans without the use of a carrier. The probe may be coupled with one or more location sensors to provide location data that is correlated with each individual frame. The term "coupled" means the sensors could be attached to the probe itself, or used to track the probe's movement without actual attachment. These sensors may provide feedback to the operator to move the probe over the tissue at the correct speed, and to start each scan row in the correct position. This will allow sufficiently complete coverage of the tissue without the need for a mechanized carrier. Alternatively, to obtain relatively uniform spacing of the frames, a speed sensor on the probe could signal the ultrasound scanning device to vary the frame capture rate to match the speed of the probe as it is moved across the tissue.

This carrier-less embodiment does not necessarily rely on the precise movement of the carrier to provide uniform spacing between the frames of a scan row in order to calculate distances between frames. Because location data are available for each frame, the location function of the viewer can use the location information of the POI frame and compare it to the location information of the RP frame, and make the requisite distance and trigonometric calculations to determine the distances from the RP to the POI.

The location sensors can be arranged in a variety of implementations. A simple inclinometer can be used to determine the orientation of the probe in two or three axes. The location of the probe face 9 could be tracked by an inertial sensor system, or a laser or infrared system, or a radio frequency local positioning system. Alternatively, a simple wheel device could be used to measure distances as well as the speed the probe is being moved over the tissue. Alternatively, an optical movement sensor, such as those commonly used in optical mice, or a laser interferometer, could be attached to the probe to track its movement. When used for scanning breast tissue in conjunction with a covering, the covering could be made of some type of fabric that is compatible with an optical movement sensor. All of these systems could use a point on the body as a reference location, such as the nipple when the system is used for breast scanning.

6. Method for Tissue Screening

The above-described devices, the probe, scanner, carrier, and viewing program, can be combined to provide a method to scan for anomalies in cellular tissue, such as cancers. The tissue is scanned, and the user views the images on a computer, rapidly scanning through the images in a "movie-like" fashion. This technique causes any anomalies in the tissue to become visible during the rapid sequential playback, as they distort or disrupt normal fibrous planes or sheets. The user can then run the images back and forth until the frame containing the anomaly is found, and the user can mark that anomaly and locate it using the location function of the program. The viewer program emits an audible and/or visual signal that marks the end of each scan row 30 or segment to allow the user to know the approximate location without having to look away from the images. The viewer can also play a continuous loop with user-selected start and end points. Follow-up studies can be performed using the location information, including a more focused ultrasound investigation, biopsy, etc.

Individual images can be manipulated using image software such as Photoshop, using filters and other manipulation techniques to enhance the appearance of the anomalies and make them more visible, including image magnification. Brightness and contrast of the frames can be adjusted. In addition, a variety of image enhancement algorithms are commonly known in the art and the viewer program allows them to be used "on the fly" as the images are displayed in rapid succession.

It is anticipated that the image review process could eventually be automated, once software is developed to identify any anomalies. If necessary, the user could then study the images to determine the accuracy of the software's identification.

Figure 11A:
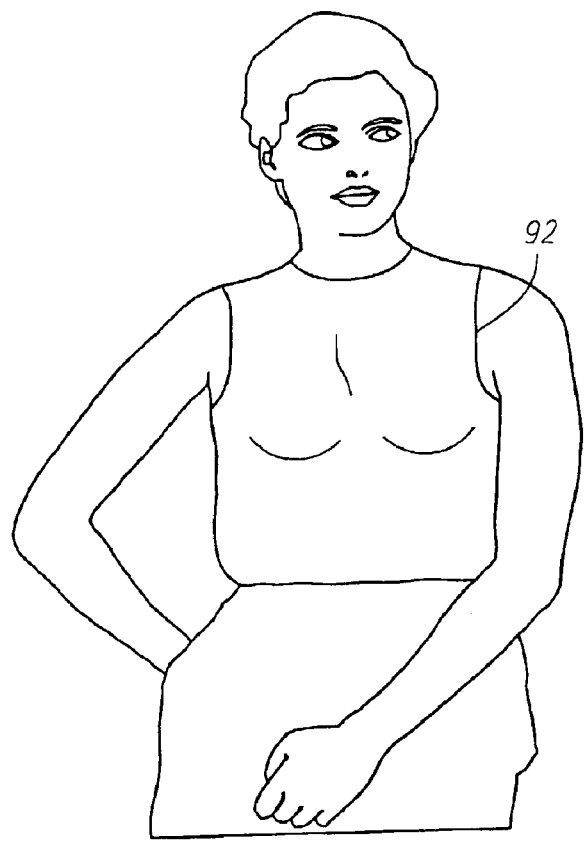
FIG. 11A is a front view of a fabric covering.
Figure 11B:
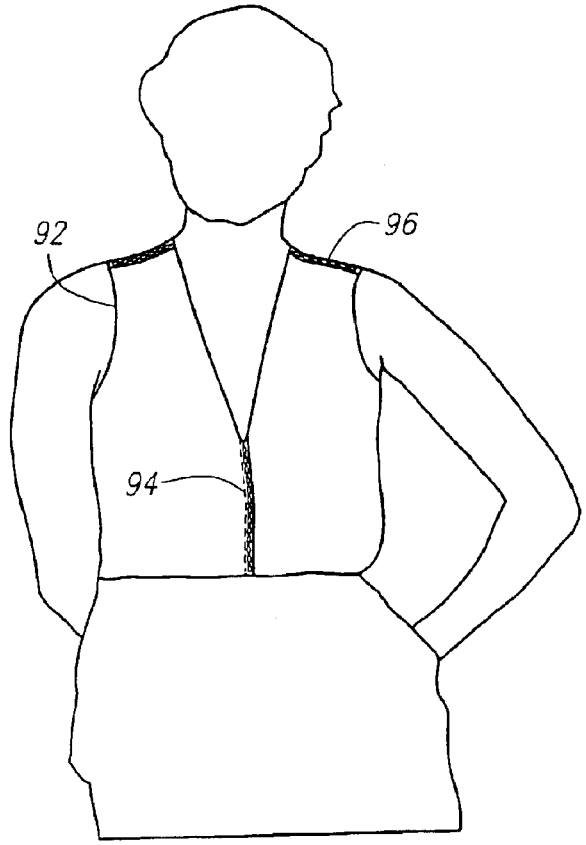
FIG. 11B is a rear view of a fabric covering.

For scanning breast tissue specifically, a preferred methodology is as follows. The mechanical probe carrier 24 is used, and depending upon the size of the probe, the breast may be scanned in strips or in its entirety, in either multiple passes or a single pass, respectively. The breast may be scanned with or without a covering. FIGS. 11A and 11B show a bra-like covering 92 that may aid in holding the breast in position for screening, as well as assisting in uniform integrity of image gathering by reducing information loss from ultrasonic shadowing. The covering 92 also provides some modesty for the patient. Current ultrasound technology requires the use of sonographic coupling agent, usually a gel, to exclude any air between the probe and the skin. Therefore, any such covering 92 would have to be capable of absorbing the gel, be relatively transparent to ultrasonic energy, and have a sufficiently loose weave so that any air trapped between the skin and the covering 92 may easily escape. The covering 92 could be pre-impregnated with the coupling agent, or the agent could be applied by the operator just prior to the scan, or both. To avoid having the patient pull a gel-soaked covering 92 over her head after the scan is completed, the covering 92 could be designed to dismantle after use. The covering 92 can be equipped with a seam in the back 94 that is constructed with chain stitching that is easily undone so that the covering 92 may be removed by slipping it off the patient's arms. The shoulder seams 96 could also be made with chain stitching to further ease removal. Since a preferred embodiment of the covering 92 is designed to be a single-use item, the covering 92 could be cut off with scissors without the need for special stitching. Zippers, hook and loop, or other fasteners could also be used to ease the putting on or removal of the covering 92, and would allow the covering 92 to be re-used. A preferred embodiment uses a stretch fabric for the covering 92, but any suitable material that can conduct or pass through ultrasonic energy could be used.

Figure 12A:
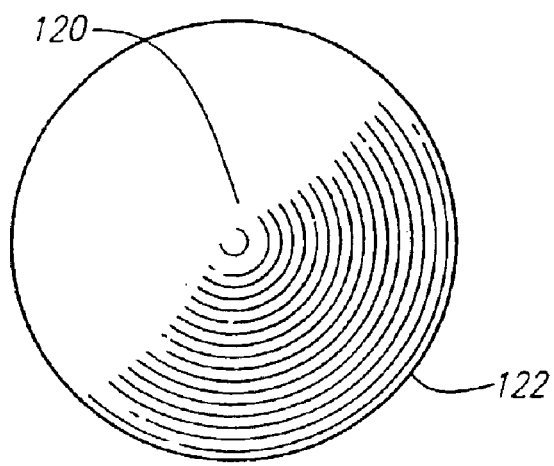
FIG. 12A is a plan view of a nipple pad.
Figure 12B:
FIG. 12B is a side view of a nipple pad.
Figure 12C:
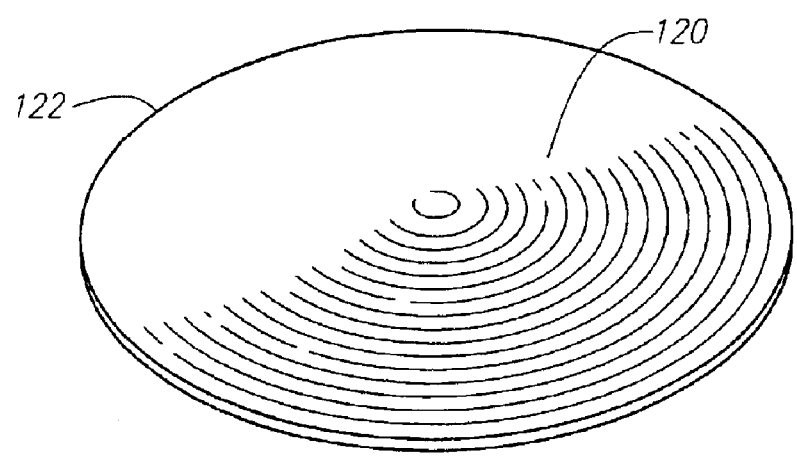
FIG. 12C is a perspective view of a nipple pad.
Figure 13:
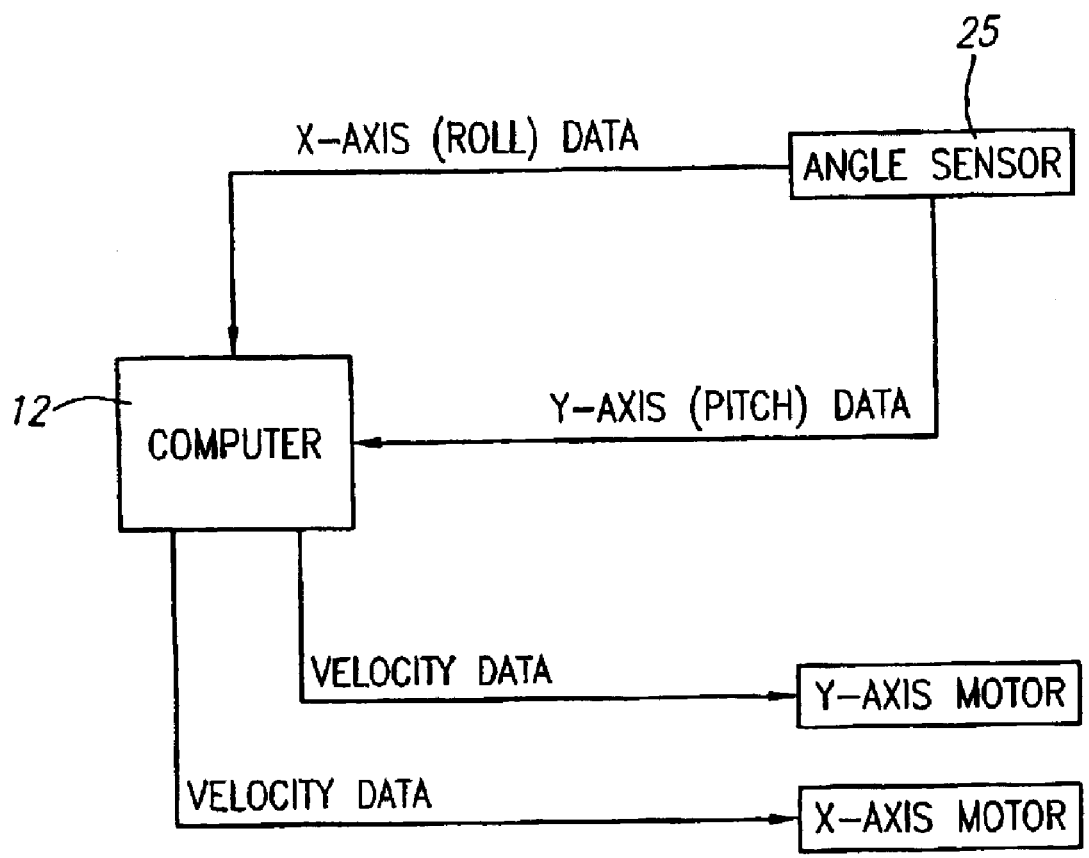
FIG. 13 is a schematic diagram showing the signals between the angle sensor, the computer and the motors.

A nipple pad 120 is placed on the patient's nipple to provide a reference point on the images. The nipple pad 120 shows up on the scan images due to its ultrasonic characteristics that distinguish it from the breast tissue. The nipple pad 120 has the added benefit of reducing ultrasonic shadowing. FIGS. 12A, 12B and 12C depict a preferred embodiment of a nipple pad 120, which is made of an ultrasonically conductive material, such as a solid gel. A preferred embodiment of the nipple pad 120 is approximately 70 mm in diameter and varies in thickness from less than 1 at the periphery to 4 mm at the center, but other sizes could be used. Larger and thicker gel pads are commercially available for isolated ultrasound scans, where offsetting the probe from the tissue is advantageous, but they are not designed to be completely traversed across their periphery during a scan. As shown in FIGS. 12A, 12B and 12C, the circular nipple pad 120 is tapered to an edge 122 about its full periphery, and has a very smooth surface. The edge 122 of the nipple pad 120 is thick enough to resist tearing, yet thin enough to allow the ultrasound probe to traverse its periphery during scanning without dislodging the nipple pad 120 or causing an ultrasonic shadow at the nipple pad's edge 122. The nipple pad 120 may be held in place by positioning it beneath the above-mentioned fabric covering 92.

As described above, the images are reviewed in a rapid sequential fashion, imparting a sense of motion through the breast tissue. The reviewer can observe or detect a disruption of the normal breast architecture through comparative image analysis or observation. The method has advantages over other ultrasound scanning techniques, including the following:

1) Parallel and contiguous images are obtained, optimizing the coverage of the breast tissue and improving the appearance of the images when viewed in a "movie-like" fashion;
2) The entire breast is imaged in a uniform and reproducible manner; and
3) The images may be maintained and reviewed singularly, in strip form, or assembled to represent an entire breast, such as 3-D reconstruction.

Accordingly, an improved ultrasonic cellular tissue screening tool is disclosed. Although embodiments and applications of this invention have been shown, it would be apparent to those skilled in the art that many more modifications are possible without departing from the inventive concepts herein. The invention, therefore, is not to be restricted except in the spirit of the appended claims.

What is claimed is:

1. A system for screening cellular tissue, comprising
   an ultrasound scanning device including an ultrasound probe that is capable of generating image data representing images of cellular tissue;
   one or more sensors coupled with the probe to determine the probe's location;
   a viewer to display the image data as images, the viewer providing a rapid sequential display of scan images;
   a pad to cover a patient's nipple, said pad being ultrasonically conductive and having different ultrasonic characteristics than breast tissue; and
   a fabric covering adapted to hold the patient's breast tissue in place during scanning, wherein the fabric is capable of absorbing an ultrasonic coupling agent and transmitting ultrasonic energy with minimal interference.

2. The system of claim 1, further comprising a receiver to receive image data from the ultrasound scanning device.

3. The system of claim 2, further comprising a recorder in communication with the receiver to store the image data.

4. The system of claim 2, further comprising a conversion device in communication with the receiver that converts the image data into a format compatible with the viewer.

5. The system of claim 1, wherein the pad is placed beneath the fabric covering and held in place by the fabric covering.

6. The system of claim 1, further comprising a carrier driven to move progressively over the cellular tissue, the probe being mounted to the carrier to generate a series of cross-sectional images of the cellular tissue that are substantially parallel to adjacent images in the series.

7. The system of claim 6, further comprising a controller in communication with the probe to sequentially activate the probe during progressive movement of the probe over the cellular tissue.

8. The system of claim 6, further comprising a computer that controls the progressive movement of the probe and is matched to the frame capture rate of the ultrasound scanner.

9. The system of claim 6, further comprising:
   a platform to steady the patient; and
   a carrier arm mounted for translational movement relative to the platform, wherein the carrier is connected with the carrier arm, and the probe is connected with the carrier, the probe being pivotally mounted relative to the carrier arm about at least one axis.

10. The system of claim 9, further comprising at least one motor controlled by at least one microprocessor to adjust the angular position of the probe.

11. The system of claim 10, further comprising an additional system for dynamically adjusting the angular position of the probe, including one or more displacement sensors proximate to the probe, wherein the one or more displacement sensors produce signals that are sent to the at least one microprocessor, which in turn produces signals that are sent to the at least one motor to adjust the angular position of the probe.

12. The system of claim 9, further comprising at least one motor controlled by at least one microprocessor to drive the probe and the carrier over the cellular tissue.

13. The system of claim 12, wherein the at least one microprocessor determines the velocity of the probe face over the skin based on the motor speed and the probe's angular position, and sends signals to the at least one motor to maintain a uniform velocity.

14. The system of claim 13, wherein the at least one microprocessor calculates the proper velocity using the following formula:

$$HV = (DV * \cos(NRA) + (FL/TI * (|\sin(ORA) - \sin(NRA)|)),$$

where:
   HV=Horizontal Velocity (of the carrier arm necessary to produce DV at the present roll angle);
   DV=Default Velocity (desired velocity of the probe face over the skin);
   FL=Fulcrum Length (distance between the roll plane pivot and the center of the probe face);
   TI=Time Interval (time in seconds between angle measurements);
   ORA=Old Roll Angle (Angle of probe along x-axis in last time increment); and
   NRA New Roll Angle (Angle of probe along x-axis at present).

15. The system of claim 12, wherein the at least one microprocessor determines the lateral position of the face of the probe during the scanning process and sends signals to the at least one motor to make position corrections.

16. The system of claim 15, wherein the at least one microprocessor calculates the lateral position corrections using the following formula:

$$YCD = (PFW * (\sin(OPA) - \sin(NPA))) - \tfrac{1}{2} PFW * (\cos(OPA) - \cos(NPA)),$$

where:
   YCD=y-axis Correction Distance (of the probe to correct for the offset from the change in y-axis angle from the previous time increment);
   PFW=Probe Face Width (width of the probe face);
   OPA=Old Pitch Angle (Angle of probe along y-axis in last time increment); and
   NPA=New Pitch Angle (Angle of probe along y-axis at present).

17. The system of claim 15, wherein the at least one microprocessor determines the starting position of the scan rows using the following formula:

$$NRO = (\cos(MPA) * PFW) - OA,$$

where:
   NRO=Next Row Offset (of the probe to avoid skip areas);
   PFW=Probe Face Width (width of the probe face);
   MPA=Maximum Pitch Angle (in the present row); and
   OA=Overlap Amount (of the contiguous rows).

* * * * *